United States Patent [19]

Rischbieth

[11] Patent Number: 5,494,049
[45] Date of Patent: Feb. 27, 1996

[54] PHYSICAL THERAPY BOLSTER

[75] Inventor: Helen J. Rischbieth, Colonel Light Gardens, Australia

[73] Assignee: Torso (Australia) Pty Ltd., Australia

[21] Appl. No.: 331,599

[22] PCT Filed: May 5, 1993

[86] PCT No.: PCT/AU93/00201

§ 371 Date: Nov. 4, 1994

§ 102(e) Date: Nov. 4, 1994

[87] PCT Pub. No.: WO93/21870

PCT Pub. Date: Nov. 11, 1993

[30]  Foreign Application Priority Data

May 5, 1992 [AU] Australia ................... PL2276

[51] Int. Cl.⁶ ............... A61G 15/00; A47C 20/00; A61F 5/00
[52] U.S. Cl. .................... 128/845; 5/630; 602/13
[58] Field of Search ................. 128/845, 846, 128/869; 602/13, 19; 5/630, 636, 640, 644

[56]  References Cited

U.S. PATENT DOCUMENTS

| | | | |
|---|---|---|---|
| 682,871 | 9/1901 | Hogan | 5/640 |
| 2,765,480 | 10/1956 | Mueller | 5/640 |
| 3,064,279 | 11/1962 | Finkle | 5/636 |
| 3,298,044 | 1/1967 | Saltness | 5/644 |
| 3,299,451 | 1/1967 | Trogdon | 5/640 |
| 3,394,414 | 7/1968 | Unger | 5/636 |
| 3,795,021 | 3/1974 | Moniot | 5/636 |
| 4,247,963 | 2/1981 | Reddi | 5/644 |
| 4,274,673 | 6/1981 | Kifferstein | 5/640 |

FOREIGN PATENT DOCUMENTS

| | | |
|---|---|---|
| 0035584A1 | 9/1981 | European Pat. Off. . |
| 2649314 | 1/1991 | France . |
| 3727353A1 | 4/1989 | Germany . |
| 2256794 | 12/1992 | United Kingdom . |

*Primary Examiner*—Michael A. Brown
*Attorney, Agent, or Firm*—Finnegan, Henderson, Farabow, Garrett & Dunner

[57]  ABSTRACT

A bolster for physical therapy procedures comprising a hollow approximately cylindrically shaped body (1), the body having a shape lying within the dimensions with a middle approximately cylindrical diameter portion of a minimum of 70 mm and a maximum of 200 mm, and having a length lying within the range of 160 mm to 500 mm, and having a wall defining the body shape which is comprised of the material and having such thickness that the shape of the bolster is substantially self restoring when the hollow body is open to atmosphere. The bolster includes ends (5, 6) which are of convex shape and include openable valves (2, 3) one at each end. The material from which the bolster is made includes both elasticity and pliability and is selected to have a "grippy" feel with respect to human skin and be relatively warm to touch.

16 Claims, 3 Drawing Sheets

PHYSICAL THERAPY BOLSTER

This invention relates to a physical therapy bolster.

It is well known to use bolsters during physical therapy procedures.

This discovery to which this invention is directed is that a bolster having significantly improved characteristics for physical therapy procedures is possible.

Hitherto, bolsters have been provided which can be in the form of for instance a folded towel, or in another case a thin walled vinyl inflated cylindrical device.

A bolster useful for the purpose has a number of quite difficult tasks to fulfil.

In one procedure, the bolster is laid along the ground and aligned with the lower spinal area of the patient so supporting the hips above the ground.

In another procedure, the bolster is located crosswise to the direction of the spine so that the thighs can be caused to rock relative to the upper part of the body around the bolster.

In another procedure, the bolster is located so as to be aligned with the spine but between the shoulder blades and supporting the upper part of the chest of the patient relative to a planar supporting base.

These are typical and by no means limiting illustrations of the types of locations that a bolster of the type being discussed is used.

Previous problems have been many with existing bolsters.

For instance, a towel can be rolled into whatever diameter cylinder is considered desirable but the shape thus formed is found to be an extremely hard generally noncompressable shape dependent of course upon the cloth from which the towel is made but consistently this is found to be extremely hard and therefore very uncomfortable for the patient.

More importantly, by having such protrusive hardness, can effect quite strong pressure points against one or more of the spinal segments which is considered to be somewhat disadvantageous.

In another form of bolster comprised of foamed polyurethane in a solid cylindrical form, the problem is that in some applications, the body force is compressed upon a smaller part of the foam so that in this case no matter what density of flexible foam is chosen, considering that the diameter of the material is necessarily limited because of the need for it to fit in relation to certain parts of the body, then the foam is collapsed to form a hard compressed segment which then becomes very uncomfortable which in turn will cause adjacent muscles to tense.

In another case, a vinyl sheet wall bolster is shaped in a cylindrical shape by internal retained air pressure.

The problem with this arrangement is that in order to ensure that the cylindrical shape will not collapse to the ground in the centre if a concentrated pressure of body weight is applied at this point, the diameter of the bolster has to be some two to three times greater than that which is considered more convenient for body location purposes.

This in turn means that the height of the bolster is a significant problem in relation to some exercises or the bolster has to be significantly deflated for these and one then gets a very spread pressure result which again is disadvantageous for a number of the physical therapy procedures where a protrusive effect of acceptable pressure is required.

The search for an appropriate bolster has been a very significant one indeed and even to find the characteristics that are most appropriate for the application has been difficult.

According to this invention then there is proposed a bolster for physical therapy procedures comprising a hollow approximately cylindrically shaped body, the body having a shape lying within the dimensions with a middle approximately cylindrical diameter portion of a minimum of 90 mm and a maximum of 150 mm, and having a length lying within the range of 160 mm to 240 mm, and having a wall defining the body shape which is comprised of a material and having such thickness such that the shape of the bolster is substantially self restoring when the hollow body is open to atmosphere.

A bolster for physical therapy procedures comprising a hollow approximately cylindrically shaped body, the body having a shape lying within the dimensions with a middle approximately cylindrical diameter portion of a minimum of 70 mm and a maximum of 200 mm, and having a length lying within the range of 160 mm to 500 mm, and having a wall defining the body shape which is comprised of a material and having such thickness such that the shape of the bolster is substantially self restoring when the hollow body is open to atmosphere.

In preference, but not essentially, the ends of the body are each of convex shape and are each of substantially semicircular shape where the diameter of the semicircle is approximately the same as the diameter of the cylindrical shape of the intermediate part of the body.

In preference and not essentially, the hollow body is openable to atmosphere through a manually controllable valve.

In preference and not essentially, the said valve comprises a valve member extending through an aperture in the wall which is located aligned with the cylindrical axis of the cylindrical intermediate part of the body and is located in a respective end.

In preference and not essentially, each of the ends has an openable valve.

In preference and not essentially, the wall defining the body of the bolster is elastic as well as being pliable.

BRIEF DESCRIPTION OF THE DRAWINGS

For a better understanding of this invention it will now be described with the assistance of drawings in which.

Figure 1:
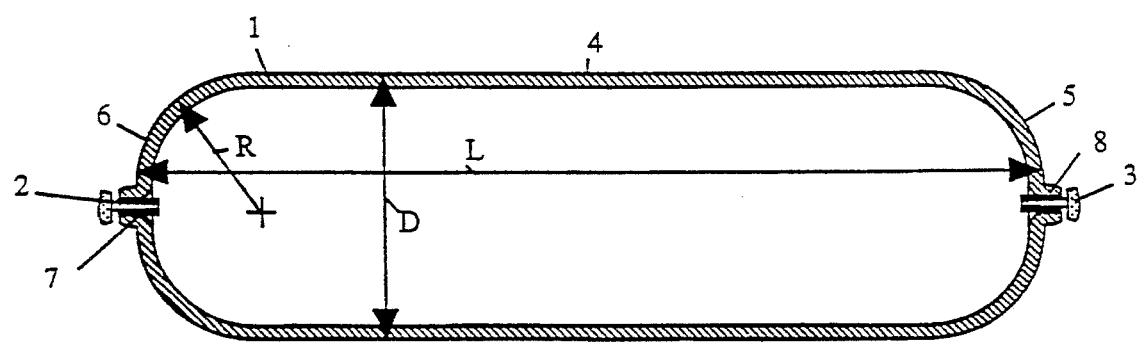
FIG. 1 is a side elevation of a bolster according to the embodiment.
Figure 2:
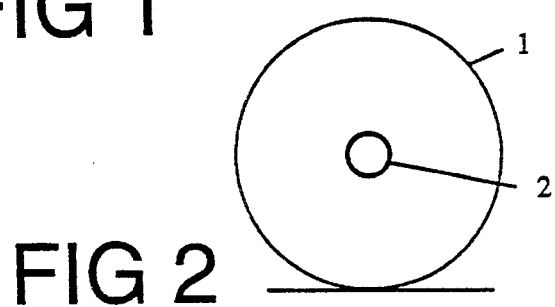
FIG. 2 is an end elevation of the bolster according to the embodiment as shown in FIG. 1.

Referring firstly to FIGS. 1 and 2 there is shown here a bolster 1 comprised of a body which is hollow and inflatable and having sealing valves 2 and 3 at respective ends of the body 1.

The body shape includes an intermediate cylindrical part 4 and at each end a hemispherical part 5 in the one instance and 6 in the other terminating in an aperture at 7 and 8 into which a valve as shown at 2 and 3 can be inserted to effect sufficient sealing of the inflatable interior of the bolster.

The diameter of the cylindrical part (D) 4 is 100 mm, and the radius of each of the approximately hemispherical ends (R) 5 and 6 is approximately 50 mm. The length (L) is 320 mms. The thickness is 3.5 mms.

The advantage of this arrangement is that as the bolster is compressed between two planar members, the compression shape at the respective ends will be substantially following a circular periphery with the result that there is a minimal hard edge effect caused to a person lying on the bolster.

The material from which the bolster is made in the embodiment is a polyvinyl chloride plastics material and molded so that the thickness of the plastic is substantial so that the wall defining the bolster body shape which is expected to be of consistently constant thickness throughout the whole of the body, is of 3.5 mm thickness but depending upon the overall length and diameter this thickness can be changed to be in the range of from 3 to 8 mms.

The polyvinyl chloride plastics is mixed with an approximately equal quantity of plasticiser and can be further modified by the addition of slight aeration such that the material provides a thick wall which provides a relatively pliable and somewhat elastic character to the material. The shape with the thickness required is achieved by rotational moulding techniques.

The effect of this is to provide a bolster having a hollow shape which will effect, when opened to atmosphere, a restoring force to the effect that in most occasions, the shape will return after being compressed, to an approximately cylindrical shape at the centre and of course with a convex shape at each end.

It is to be emphasised that the material is plastic and has creep characteristics so that if the pressure is kept on for a reasonable period of time, any restoration of the shape will be slower.

One advantage of providing this small quantity of aeration into the polyvinyl chloride mixture is that this provides a warmer feel to the bolster than would be provided by the same material without the aeration. It has been found however to be more difficult to acheive consistent result using aeration so that this is now less preferred.

As an incidental further advantage, the surface of the bolster is provided with a roughened texture which is also considered to be more skin like and therefore if used against bare skin, less objectionable. The texture also helps keep the bolster in place due to the "grippy" nature of the roughened texture.

The problem to which the invention has related has been to find a bolster which can provide characteristics which while being the same time comfortable can nonetheless still provide an adequate intrusive effect.

Accordingly we will now describe characteristics of the embodiment as presently manufactured by using rotational moulding and will further then indicate typical ranges that are considered to be acceptable for the purposes of achieving best advantages from an invention.

Figure 3:
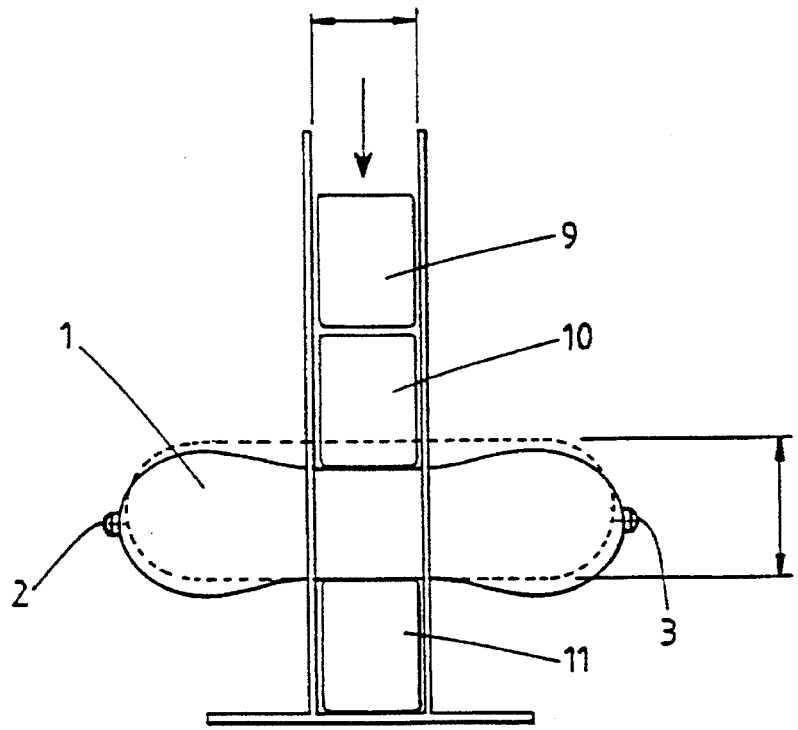
FIG. 3 is a schematic arrangement showing a testing rig for determining some of the characteristics of the embodiment.

In FIG. 3, the bolster 1 is filled with air at atmospheric pressure and the end valves 2 and 3 are sealed.

The weights 9 and 10 are 75 mm wide so that they are bearing as shown at 9 on the bolster 1 with this link.

The underneath side of the bolster 1 is also supported by a weight having the same dimensions shown at 11.

Each of the weights is 3.835 kgs.

A first single weight depressed the bolster from the 100 mm nominal diameter to 70 mms.

Two weights providing therefore a total weight of 7.67 kgs depressed the bolster to leave a gap of 63mms and a total weight of 11.505 kgs depressed the bolster to 58 mms.

Figure 4:
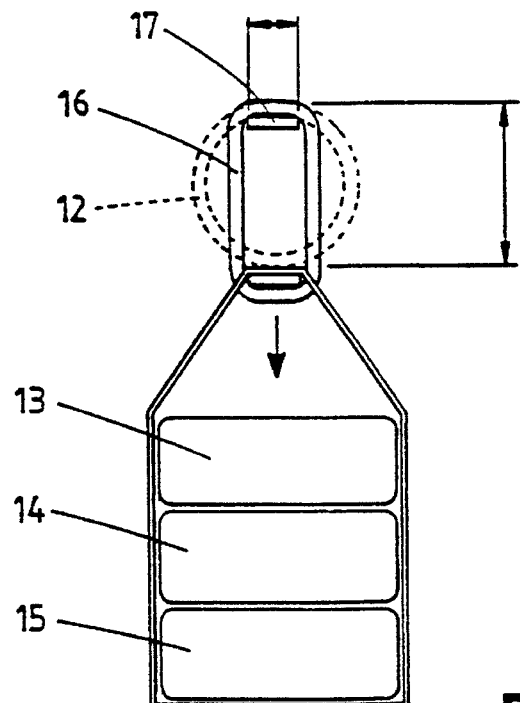
FIG. 4 is a further testing rig for determining further characteristics of the embodiment.

Referring now to FIG. 4, the bolster material shown nominally in cross section at 12 is a piece cut from the embodiment having a nominal outside diameter of 100 mm being a 20 mm wide ring cut from the embodiment and this is captured in a sling so that each of the weights shown at 13, 14 and 15 each of which weights 3.85 kgs can be applied to stretch the 20 mm ring of bolster material shown at 16.

Accordingly, a single weight of 3.85 kgs stretched the bolster ring 40 mm, 7.65 kgs 52 mm, and 11.505 kgs 65 mm.

The width at 17 of the member from which the ring is supported and the lower member are each of 35 mm width.

Figure 5:
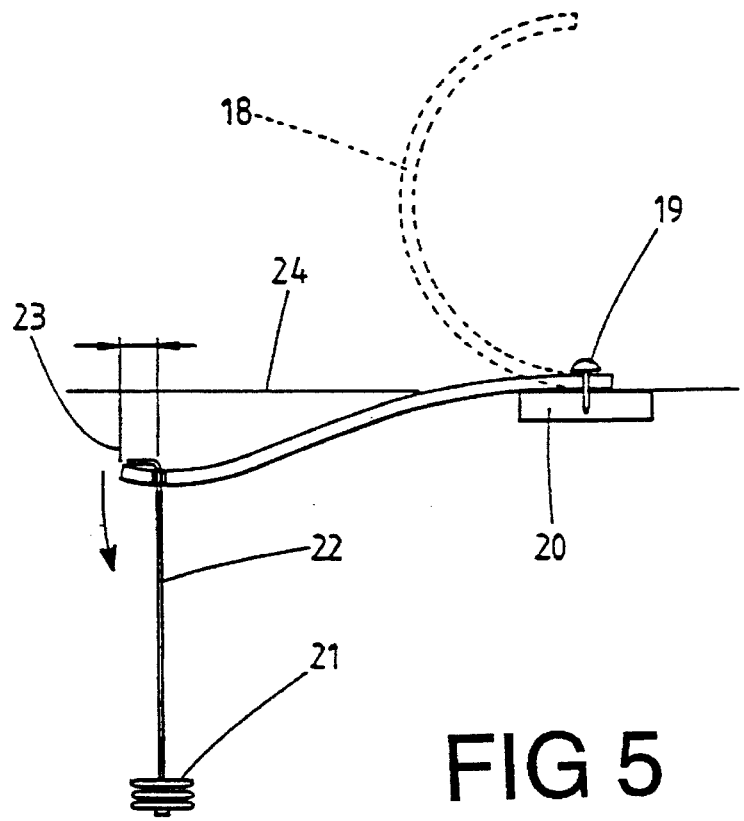
FIG. 5 is a further testing rig for testing characteristics of the embodiment.

Referring to FIG. 5, which is a cantilever flex test, the piece of bolster used is shown at 18 which is a piece of the bolster wall, that is, taken from the intermediate cylindrical part and it is of 20 mm wide and of course 100 mm nominal outside diameter.

This was then pinned by pin 19 onto a 35 mm wide support at 20 and weights at 21 were hung where the pin 22 was inserted through the end of the bolster material piece through 2 mm hole 10 mm in from the end at 23.

The results are that for a first 2.7 gms of weight, the material at rest with merely the hook itself located in it was located at alignment 24 and this was then successively lowered by the first 2.7 gms effecting 32 mms lowering, 5.4 gms 45 mm, 8.1 gms 57 mms, 10.8 gms 66 mms, 13.5 gms 68 mms, 16.2 gms 74 mms, and finally 18.9 gms 83 mms.

Figure 6:
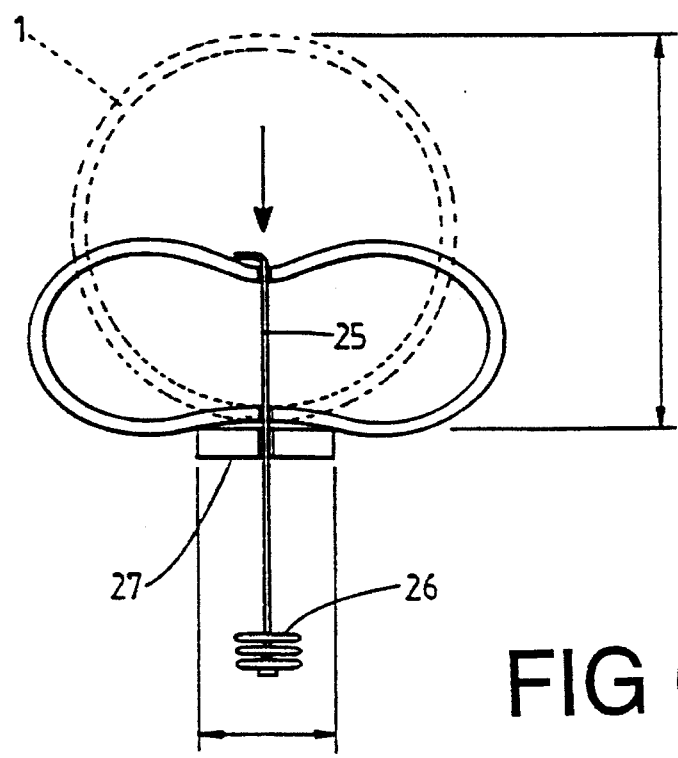
FIG. 6 is a further testing rig for determining characteristics of the embodiment.

Finally referring to FIG. 6, this is a test once again taking a 20 mm wide ring but in this case the nominal shape of the ring is fully circular as in the example of FIG. 4, and a wire hook at 25 passes through a 2 mm hole and the weights at 26 are brought in successively with the bolster ring flattening over the 35 mm width base support at 27.

In this case the 11.3 gms causes 5 mm lowering from the 100 mm nominal diameter position and in sequence 22.6 gms 15 mms, 33.9 gms 25 mms, 45.2 gms 35 mms, 56.5 gms 50 mms, 67.8 gms 58 mms and finally 79.1 gms 70 mms.

These tests illustrate the characteristics of the material providing the wall of the bolster of the embodiment given.

As an example of the range which is considered to be useful, in the test in FIG. 3, there was seen to be from 3 to 8 mms per kilo applied and a preferred range would be from 2 to 10 mms per kilo applied.

In the test in FIG. 4, there was a range from 5 to 10 mms per kilo applied and this could be extended in other preferred examples from 2.5 to 15 mms per kilo applied.

In the cantilever flex test of FIG. 5, there was a range of travel of 5 to 10 mms per gram applied and this could be extended to 2.5 to 15 mms per gram applied.

Finally, for the ring compression test in FIG. 6, the range of travel is from 0.5 to 1 mm per gram applied and this could be extended to 0.25 to 1.5 mm per gram applied.

The total weight of material used in the embodiment is 450 gms of material.

This could typically extend from 400 to 460 gms.

Various dimensional changes can be incorporated but a minimum total length of 200 mm to a maximum 500 mm the mearurement being taken from the outerside of the bolster and at the extreme end of the convex shape but not including any part providiing the valve means indicate the more preferred range with 320 mm being the most preferred.

The length is chosen so that it can be located comfortably but still protrusively along an upper part or a lower part of the spine of a patient. In relation to the total range of diameters, a minimum of 90 mm to a maximum 150 mm for both the intermediate cylindrical part and the dome shape of the ends would appear to define the most desirable range.

The body bolster is a body conditioning tool (or back conditioning) that can be utilized in therapy to create postural changes. By having a person drape into extension over the bolster (either lengthways or crossways) the spinal joints can then be stretched beyond their developed structural limit as the muscles relax.

The advantage of using the bolster according to this invention as opposed to other more intrusive-devices such as a rolled up towel or hair spray tin or polystyrene roll, is that it is elastic as well as pliable and its intrusive nature characteristic allows the user to relax over the bolster such that the muscles appear to be able to relax to an extent that is not seen using other forms of support.

Neurologically the body is conforming to a new shape such that new postures can then be developed from this. This can allow for opened up areas that can normally never be exposed to such an effect.

Another main therapeutic use is to place the bolster underneath the pelvis whilst laying supine. In this position the user can learn to roll their pelvis over or about the bolster in order to learn to control pelvic movement in relation to leg/hip control as for gait and running patterns, and also to develop lumbo-sacral mobility and awareness and again the effectiveness comes from the described characteristics of the bolster according to this invention.

The bolster according to the invention can be variously inflated but according to one method of use which is used for a first user introduction the bolster is open to atmosphere and pressure is applied from opposite sides to bring the sides together medially the ends at which position the bolster is closed to atmosphere. This creates a wide and long support which none the less will still keep a person resting on this and this provides a "low strain" starting point for therapeutic use (in which the bolster stops rolling from occuring).

From the above it will be seen that the bolster is a musculo-skeletal conditioning tool for use anywhere about the torso for instance, vertebrae of the spine, ribs, shoulder, girdle, pelvic girdle, hips and all the muscles that attach to these areas.

The bolster performs two main functions namely (a) postural support in sitting situations and (b) musculo-skeletal as a conditioning tool for the torso in lying, sitting or reclining situations for the purposes of (1) stretching the soft tissues, (2) exercising for mobility and/or strengthening purposes, (3) developing, maintaining or enhancing neurological and kinaesthetic awareness of the musculo-skeletal system of the torso as well as proprioception, (4) and the ability to improve the quality and efficiency of the functional physical performance of the torso and/or the entire musculo-skeletal system with the bolster as a tool for learning about the appropriate capabilities.

When the bolster is used as a postural support in sitting situations, the bolster because of its design may be placed in between the body and surface of the chair or seat in the following way: transversely or longitudinally anywhere along the length of the spine (between the cranium and the pelvis) and ribs (for upright chairs and/or reclining). The usual position for postural support in a chair is transversely at the lumbar spine level or cervical spine. However, the bolster with different inflation levels can be used in different ways for instance, when used in the longitudinal position along part of the length of the spine, the ends of the bolster, when only partially inflated, are designed to intrude and so provide more support to the spine in these areas as well as creating protrusions over which the spine can be stretched; transversely or antero-posteriorly beneath the pelvis, on a chair or seat, to enable a pelvic position in sitting that is more anteverted. This has the benefit of providing more support for the torso by aligning the natural curves of the spine in the upright position, against gravity, so reducing the muscular effort required in unsupported situations which is the case when there is no back on the chair.

When the bolster is used as a conditioning tool, the bolster may be used in any sitting, reclining or lying position where in each case, the rolling capability available allows for dynamic postures which in turn reduces the development of stiffness of the musculo-skeletal system of the body and reduces muscle fatigue by allowing/using different muscle groups to act in turn as opposed to the habitual muscle groups.

Finally, the bolster by reason of the control valve can be fully deflated and then wrapped into a small volume for transport by users.

As an illustration of the effectiveness of the embodiment and the invention, several case histories will now be given illustrating the way in which the bolster has provided significant beneficial results which would not appear to be available other than by use through the invention.

Another use in this mode is to control the extension of the spine. The reason for this is that when the bolster is used in the transverse location beneath the supine body facing upwardly the bolster located between the pelvis and cranium at selected positions along the spine provides a conforming shape allowing for rolling and or static hold freedom across an area such that again intrusive forces are spread across the susceptible tissue of the user while providing adequate intrusion for the purpose of providing the stretch required for training and therapy of the human body.

EXAMPLES

Example 1

Mrs B. M. presented with a twelve month history of substantial pain in her left shoulder joint which was diagnosed as capsulitis with a marked tension/pain pattern throughout her upper left torso quadrant.

She had previously received extensive physio therapeutic treatment with traditional devices according to best techniques available by alternate methods. Mrs B. M. was unable because of this pain to drive a car for any continuous period of longer than several minutes which seriously devoided her employer ability.

Mrs B. M. was provided with a bolster in accord with the preferred embodiment and commenced using this firstly so that she could be seated on the bolster allowing her pelvis to rotate and this in turn allowed her, with the comfort and relaxation provided by the softness of the bolster, to feel different muscles that were unevenly tense and thus in turn distinguished the muscles controlling her pelvis as compared to the remainder of her torso. In addition, Mrs B. M. commenced using the bolster according to the preferred embodiment longitudinally along the spine when seated in the motor vehicle, the alignment and contact being at the mid thoracic level which resulted in her stretching and in fact allowing her to stretch and spread in a comfortable way the front part of the torso. Within two months Mrs B. M. was able to revert to being able to drive all day subject to using the bolster in conjunction with the car seat in a longitudinal position behind the spine.

Example 2

Dr K., a seventy-one year old medical specialist, presented with a low lumbar damaged disc (at L3/4) and had received extensive specialist treatment over the past forty-six years in an attempt to alleviate suffering from the injury. He presented because he still suffered significant back pain after standing stationary of periods longer than five minutes and that movement however helped somewhat to ease the aching. Previous treatment had included directions to conduct back exercises for mobility and strengthening but these have not been carefully followed and used for reasons which incorporated discomfort and therefore motivation.

Dr K. commenced using the bolster according to the preferred embodiment and in conjunction with training as to the manner of use which included all of the various techniques previously described which includes use of the bolster longitudinally along the spine, sitting on the bolster with this elongate between the buttocks, and transversely behind the lumbar area and a seat, Dr K. found firstly that he no longer needed to remember to conduct exercises but started to do these implicitly as a part of the use of the bolster and specifically because of the design and features of the bolster, these allowed relaxation and indeed to motivation to use the bolster.

The results after six months from his first presenting, was that Dr K. had received a lower level of pain than had hitherto been achieved with any previous treatment.

Example 3

Mrs B. presented with symptoms of stress and muscle tension since a birth of a first baby twelve months previously. This included constant aching and tightness in her neck and shoulders. The bolster was introduced as a part of a relaxation and stress management program firstly as a lumbar support and vertical spinal support and a positioning tool for breastfeeding so that her spine and body was better aligned during this activity. The result was significantly less strain and ache in her neck and shoulders which can be directly and uniquely attributed to the features of the bolster according to the preferred embodiment. The response from Mrs B was of great relief and excitement in so far that breastfeeding activity became pleasurable because of the now newfound success and ease of this activity which had apparently not been available by any other technique previously. A particular value of the bolster during the breastfeeding was the use of this in an intrusive manner longitudinally behind her lumbar spine which had the result of organising her entire torso posture further forward. This promoted her postural awareness and also enabled her to view the child during the breastfeeding which has previously not been comfortably available.

Example 4

Mr A. C. presented at fifty-nine years old with suffering pain in his left leg relating to a degenerative condition of his lumbar spine. This has been a problem for twelve years and was especially aggravated by walking and playing of lawn bowls. Mr A. C. also suffered a mild version of Parkinson disease. A clinical assessment was that he had poor movement patterns which were exacerbated by the Parkinsons disease and muscle tension habits aggravated by his lumbar spine which contributed to the leg pain. Specific use of the bolster again in providing exercise patterns according to the previous descriptions resulted in Mr A. C. learning to differentiate his pelvis relative to the rest of his trunk and how to rotate this through his trunk during his gait—both of which ideas were elusive. The use of the bolster contributed significantly to our ability to change the muscle tension and learned muscle patterns with the result that he was able to relax on the bolster, particularly due to its comfortable and elastic feel and develop the confidence necessary to move with complex movements of the pelvis in space. As an immediate result of this after four months of treatment was that Mr A. C. was able to return to playing of lawn bowls without apparent difficulty and was able to commence walking with minimal pain and small difficulties.

These examples have been taken from a number of examples of equivalent value but illustrate these very significant advantages of the feature of the bolster according to the invention.

This then describes in fairly specific ways the characteristic of a bolster which has been shown to provide significant advantages over bolsters that have been previously available.

I claim:

1. A bolster for physical therapy procedures comprising a hollow, airtight body having an approximately cylindrically shaped intermediate part having an axis and having opposed ends, the interior of the body being selectively openable to the atmosphere, the body having a shape with the intermediate approximately cylindrical part having a diameter lying within the range of a minimum of 70 mm and a maximum of 200 mm and having a length lying within the range of 160 mm to 500 mm, and having a wall defining the body shape which is comprised of a material and having such thickness such that the shape of the bolster is substantially self restoring when the interior of the hollow body is open to atmosphere.

2. A bolster for physical therapy procedures comprising a hollow, airtight body having an approximately cylindrically shaped intermediate part having an axis and having opposed ends, the interior of the body being selectively openable to the atmosphere, the body having a shape with the intermediate approximately cylindrical part having a diameter lying within the range of a minimum of 90 mm and a maximum of 150 mm, and having a length lying within the range of 160 mm to 240 mm, and having a wall defining the body shape which is comprised of a material and having such thickness such that the shape of the bolster is substantially self restoring when the interior of the hollow body is open to atmosphere.

3. A bolster for physical therapy procedures as in either of claim 1 or 2 further characterized in that the ends of the body are each of convex shape.

4. A bolster for physical therapy procedures as in either of claims 1 or 2 further characterized in that the ends of the body are each of substantially semicircular shape where the diameter of the semicircle is approximately the same as the diameter of the cylindrical shape of the intermediate part of the body.

5. A bolster for physical therapy procedures as in claim 1, further characterized in that the hollow body is openable to atmosphere through a manually controllable value.

6. A bolster for physical therapy procedures as in claim 1, further characterized in that the hollow body is openable to atmosphere through a manually controllable valve, the said valve comprising a valve member extending through an aperture in the wall which is located aligned with the cylindrical axis of the cylindrical intermediate part of the body in a respective end.

7. A bolster for physical therapy procedures as in claim 1, further characterized in that the hollow body is openable to atmosphere through at least one of manually controllable valves positioned at each end of the body, each said valve comprising a valve member extending through an aperture in the wall which is located aligned with the cylindrical axis of the cylindrical intermediate part of the body in a respective end of the body.

8. A bolster for physical therapy procedures as in claim 1, further characterized in that the wall defining the body of the bolster is, by reason of the material from which it is made, its thickness and shape, elastic as well as pliable.

9. A bolster for physical therapy procedures as in claim 1, further characterized in that the wall defining the body of the bolster is comprised of a polyvinyl chloride plastics material which is molded so that the wall defining the bolster body shape is of substantially constant thickness throughout the whole of the body, which thickness is within the range of 3–8 mm.

10. A bolster for physical therapy procedures as in claim 1, further characterized in that the wall defining the body of the bolster is comprised of a foamed polyvinyl chloride plastics material which is molded so that the wall defining the bolster body shape is of substantially constant thickness throughout the whole of the body, which thickness is within the range of from 3–8 mm.

11. A bolster for physical therapy procedures as in claim 1, further characterized in that the material is of a type and thickness such that in the test described with respect to the arrangement as shown in FIG. 3 herein, the intermediate part of a nominal 100 mm OD body is caused to deflect a distance of about 2–10 mm per kilogram of applied weight when the interior is closed to the atmosphere and is at atmospheric pressure in the undeflected state.

12. A bolster for physical therapy procedures as in claim 1, further characterized in that the material is of a type and thickness so that in the test described with respect to the arrangement as shown in FIG. 4 herein, a 20 mm ring cut from the intermediate part of a nominal 100 mm OD body is caused to elongate a distance of about 2.5–15 mm per kilogram of applied weight.

13. A bolster for physical therapy procedures as in claim 1, further characterized in that the material is of a type and thickness such that in the test described with respect to the arrangement as shown in FIG. 5 herein, a one-half ring section 20 mm wide cut from the intermediate part of a nominal 100 mm OD body is caused to deflect 0.25–1.5 mm per gram of applied weight.

14. A bolster for physical therapy procedures as in claim 1, further characterized in that the material is of a type and thickness such that in the test described with respect to the arrangement as shown in FIG. 6 herein, a 20 mm wide ring section cut from the intermediate part of a nominal 100 mm OD body is caused to deflect 0.25–1.5 mm per gram of applied weight.

15. A bolster for physical therapy procedures as in claim 1, wherein when the interior is inflated and closed to the atmosphere, the body can rollably support the pelvis of a patient.

16. A bolster for physical therapy procedures as in claim 1, wherein when the interior is partially deflated and closed to the atmosphere, the body will support the pelvis of a patent against rolling.

* * * * *